United States Patent [19]

Christiansen et al.

[11] Patent Number: 5,100,882
[45] Date of Patent: Mar. 31, 1992

[54] ANTIANDROGENIC SULFONYLSTEROIDOFURANS

[75] Inventors: Robert G. Christiansen, Schodack; Malcolm R. Bell, East Greenbush; Virendra Kumar, Colonie, all of N.Y.

[73] Assignee: Sterling Drug Inc., New York, N.Y.

[21] Appl. No.: 541,656

[22] Filed: Jun. 21, 1990

[51] Int. Cl.$^5$ ............... C07J 51/00; A61K 31/58
[52] U.S. Cl. .................................. 514/172; 540/48
[58] Field of Search ....................... 514/172; 540/48

[56] References Cited

U.S. PATENT DOCUMENTS

| | | | |
|---|---|---|---|
| 3,146,186 | 9/1964 | Orr | 540/48 |
| 3,432,486 | 3/1969 | Minato | 540/48 |
| 4,684,636 | 8/1987 | Christiansen et al. | 540/48 |

OTHER PUBLICATIONS

Chemical Abstracts vol. 111, 1989 p. 2921F-Formula Index.
Hadley, Endocrinology [Prentice Hall, Englewood Cliffs, N.J., 1984] pp. 386-390.
Orr et al., Steroids, vol. 3, No. 1, pp. 1-12, 1964.
Stefanovic et al., Tetrahedron Letters No. 36, pp. 3311-3312, 1971.

Primary Examiner—Mukund J. Shah
Assistant Examiner—E. C. Ward
Attorney, Agent, or Firm—Theodore C. Miller; Paul E. Dupont

[57] ABSTRACT

5'-Alkylsulfonylsteroido[3,2-b]furans, for example 5'-methylsulfonyl-5α-pregn-2-en-20-yno[3,2-b]furan-17β-ol having the structural formula,

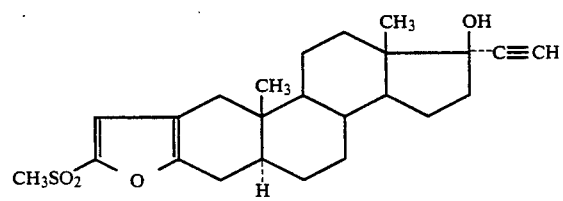

which are useful as antiandrogenic agents, and processes for preparation, method of use and compositions thereof are disclosed.

14 Claims, No Drawings

ANTIANDROGENIC SULFONYLSTEROIDOFURANS

BACKGROUND OF THE INVENTION

1. Field of the Invention

The invention relates to 5,-alkylsulfonylsteroido[3,2-b]furans, which are useful as antiandrogenic agents, and processes for preparation, method of use and compositions thereof.

2. Information Disclosure Statement

Christiansen et al U.S. Pat. No. 4,684,636 issued Aug. 4, 1987 describes antiandrogenic sulfonylsteroidopyrazoles including as EXAMPLE 1 the compound having the structural formula

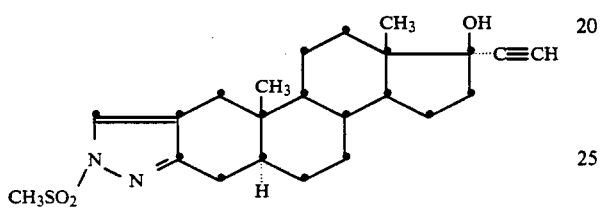

which showed relative binding affinities of 2.1 at 1 hr. and 0.09 at 18 hr. in the rat prostate androgen receptor competition assay and an $AED_{50}$ value of 14 mg./kg. orally in the test for antiandrogenic activity in the castrated immature male rat.

Minato U.S. Pat. No. 3,432,486 issued Mar. 11, 1969 describes 4'-methyl-5α-androst-2-eno[3,2-b]furan-17β-ol acetate ester having the structural formula

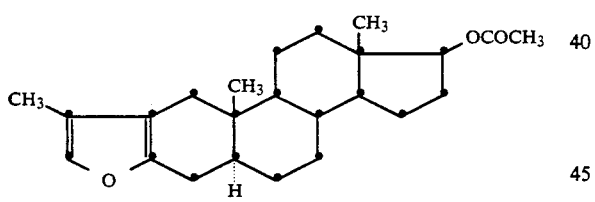

and states that it is "useful as [an] antiestrogenic agent". The corresponding 17β-ol compound is also described, but no utility thereof is shown.

Orr et al. (Steroids, vol. 3, no.1 pp. 1–12, 1964) describes 5'-methyl-5α-androst-2-eno[3,2-b]furan-17β-ol having the structural formula

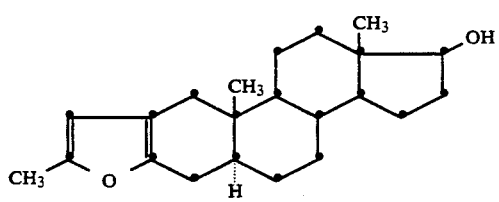

No utility is described.

Stefanovic et al. (Tetrahedron Letters No. 36, pp. 3311–3312, 1971) describes 5'-$R_2$-estra-1(10),2,4-trieno[3,2-b]furan-17-one having the structural formula

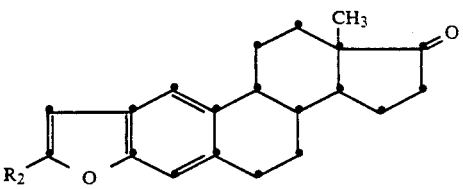

wherein $R_2$ is n-$C_3H_7$, n-$C_4H_9$, n-$C_6H_{13}$, $HOCH_2CH_2$ or $C_6H_5$ and the corresponding 17β-ol wherein $R_2$ is n-$C_3H_7$ but does not describe any biological property thereof.

SUMMARY OF THE INVENTION

In a first composition of matter aspect the invention is a compound having the structural formula

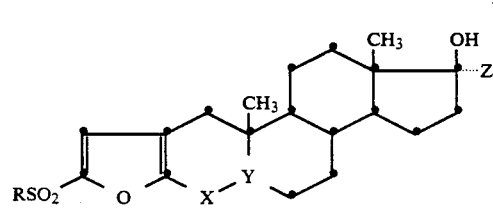

Formula I wherein
R is $CH_3$, $CH_3CH_2$, $CH_3CH_2CH_2$ or $(CH_3)_2CH$;
X-Y is

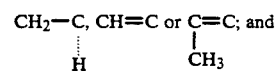

Z is H, $CH_3$, $CH_2CH_3$, C≡CH or CH=$CH_2$.

The compounds of Formula I are useful as antiandrogenic agents.

In a first process aspect the invention is the process of preparing a compound of Formula I which comprises oxidizing with a peroxide the corresponding compound having the structural formula

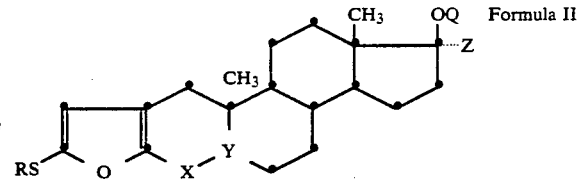

Formula II wherein Q is H; or oxidizing with a chromium oxide the corresponding compound of Formula I wherein Z is H and alkylating with the corresponding Z'-Li or Z'-MgCl or Z'-MgBr wherein Z' is $CH_3$, $CH_2CH_3$, C≡CH or CH=$CH_2$ the resulting compound having the structural formula

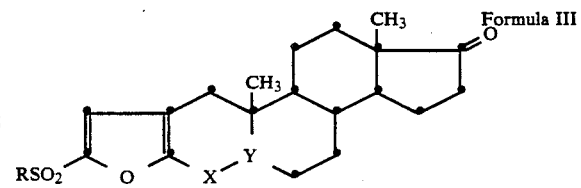

Formula III to form the corresponding compound of Formula I wherein Z is Z'; or hydrogenating with a palladium catalyst the corresponding compound of Formula I wherein Z is C≡CH to form the corresponding compound of Formula I wherein Z is CH=C₂ or CH₂CH₃.

In a second process aspect the invention is the process for effecting an antiandrogenic response in a mammal which comprises administering to the mammal an antiandrogenically effective amount of a compound of Formula I.

In a second composition of matter aspect the invention is a composition which comprises an antiandrogenically effective concentration of a compound of Formula I and a pharmaceutically acceptable vehicle.

DETAILED DESCRIPTION OF THE INVENTION INCLUSIVE OF THE PREFERRED EMBODIMENTS

Preparation of the Compounds

In the preparative process aspect of the invention and the following description "corresponding" means that the variables of the reactants used to prepare a particular compound of Formula I are the same as those of the compound of Formula I.

The peroxide for oxidizing a compound of Formula II to the corresponding compound of Formula I is any peroxide capable of oxidizing RS to RSO₂ and is preferably a peroxyacid, most preferably m-chloroperbenzoic acid or potassium peroxymonosulfate (OXONE). The preferred chromium oxide for oxidizing a compound of Formula I wherein Z is H to the corresponding compound of Formula III is pyridinium chlorochromate. Alternatively the compound of Formula III is prepared by oxidizing the corresponding compound of Formula II wherein Q and Z taken together are a bond, that is wherein the 17-substituent is keto, with a peroxide, preferably potassium peroxymonosulfate (OXONE). All three oxidations are carried out in an inert solvent at a temperature in the range from 0° C. to 100° C. Alkylation of the compound of Formula III with Z'-Li, Z'-MgCl or Z'-MgBr, which are known compounds, is carried out in an ethereal solvent at a temperature in the range from −100° C to 100° C. The preferred palladium catalyst for hydrogenating C≡CH to CH=CH₂ is palladium on strontium carbonate. The preferred solvent therefor is pyridine. The preferred palladium catalyst for hydrogenating C≡CH to CH₂CH₃ is palladium on carbon. The preferred solvent therefor is ethanol. Both hydrogenations are carried out at a temperature in the range from 0° C. to 100° C.

The compound of Formula II wherein Q is H is prepared by reaction of the corresponding compound having the structural formula

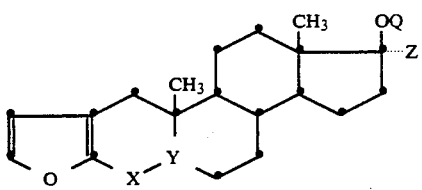

wherein Q is an ether protecting group with the corresponding R-S-S-R in the presence of an alkyllithium or aryllithium and a tertiary amine in an ethereal solvent to afford the corresponding compound of Formula II wherein Q is an ether protecting group. The preferred ether protecting group is tetrahydropyranyl, which is introduced by reaction of the corresponding compound of Formula IV wherein Q is H with dihydropyran in an inert dry solvent with an acid catalyst, for example, p-toluenesulfonic acid, and is removed by hydrolysis in an inert aqueous solvent with an acid catalyst, for example, p-toluenesulfonic acid. The preferred alkyllithium or aryllithium is butyllithium. The preferred tertiary amine is tetramethylethylenediamine. The preferred ethereal solvent is ether. The reaction is carried out at a temperature in the range from −50° C. to 100° C.

The compound of Formula II wherein R is CH₃ and Q and Z taken together are a bond is alternatively prepared from the corresponding compound of Formula IV wherein Q is H and Z is H by reaction with dimethylsulfoxide and trifluoroacetic anhydride in an inert solvent, preferably dichloromethane, in the presence of a tertiary amine, preferably diisopropylethylamine, at a temperature in the range from −100° C. to 100° C.

The compound of Formula IV wherein Q is H is prepared by reduction-dehydration of the corresponding compound having the structural formula

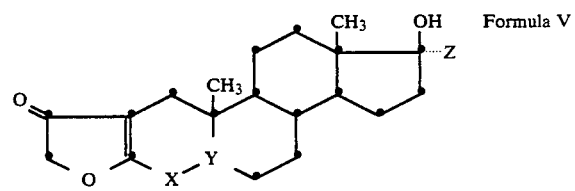

with a dialkylaluminum hydride in an inert solvent at a temperature in the range from −50° C. to 100° C. The preferred dialkylaluminum hydride is diisobutylaluminum hydride.

The compound of Formula V is prepared by cyclization of the corresponding compound having the structural formula

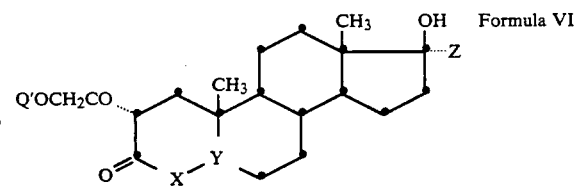

wherein Q' is an ether protecting group, preferably tetrahydropyranyl, with an acid catalyst, preferably p-toluenesulfonic acid, in an aqueous alcoholic solvent, preferably 95% ethanol, at a temperature in the range from 0° C. to 100° C.

The compound of Formula VI is prepared by acylation of the known corresponding compound having the structural formula

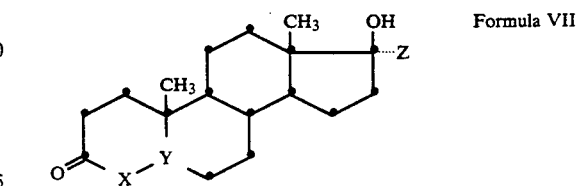

with the known Q'OCH₂COOQ" wherein Q" is methyl or ethyl and a strong base, preferably sodium hydride, in an inert solvent, preferably dimethylformamide, at a temperature in the range from 0° C. to 100° C.

In the examples set forth below structures of products are inferred from structures of starting materials and expected courses of preparative reactions. Structural confirmation and estimation of purity of starting materials and products are measured by one or more of melting temperature range (m.r.), elemental analysis, infrared (IR) spectral analysis, ultraviolet (UV) spectral analysis, nuclear magnetic resonance (NMR) spectral analysis, gas chromatography (GC), high pressure liquid chromatography (HPLC) and thin layer chromatography (TLC).

EXAMPLE 1

A. Under nitrogen with stirring at room temperature solution of 17β-hydroxy-5α-androstan-3-one (the compound of Formula VII wherein X-Y is

and Z is H, 145.2 g.) in dry dimethylformamide (500 ml.) was added slowly to a suspension of sodium hydride (60%, 48 g.) in dry dimethylformamide (100 ml.). A solution of methyl glycolate tetrahydropyranyl ether (130.5 g.) in dry dimethylformamide (100 ml.) was then slowly added. After continued stirring overnight methanol (50 ml.) was added slowly. The resulting mixture was poured into ice-water (4 l.). The resulting solution was filtered and the filter pad was washed with water. Neutralization of the filtrate with hydrochloric acid (6N) gave a white crystalline solid, which was collected by filtration, washed with water and dried, affording 17β-hydroxy-2α-{[(tetrahydro-2H-pyran-2-yl)oxy]acetyl}-5α-androstan-3-one (the compound of Formula VI wherein Q' is tetrahydropyranyl, X-Y is

and Z is H; 206 g, 96% yield). Recrystallization of part (15.0 g.) of the product from cyclohexane gave a white crystalline solid (12.0 g.) having m.r. 128°-131° C.

B. A solution of part (190.6 g.) of the product of part A of this example and p-toluenesulfonic acid (15.0 g.) in ethanol (95%, 600 ml.) was heated under reflux for 30 minutes, then poured into ice-water. The resulting yellow solid was collected by filtration, washed with water and dried, affording 17β-hydroxy-5α-androst-2-eno[3,2-b]furan-4'(5'H)-one (the compound of Formula V wherein X-Y is

and Z is H) as a pale orange crystalline solid (122.6 g., 84% yield). A sample of the same compound from a smaller scale preparation had m.r. 114°-118° C.

C. Under nitrogen with stirring at 0° C. a solution of diisobutylaluminum hydride in toluene (1.5M, 542 ml.) was added dropwise to a solution of part (122.0 g.) of the product of part B of this example in dichloromethane (1 l.). Stirring was continued for 15 minutes after completion of the addition. The resulting mixture was poured into ice-water containing acetic acid (300 ml.). The dichloromethane layer was separated, washed with water and then with saturated aqueous sodium bicarbonate solution, dried over magnesium sulfate and stripped of dichloromethane. A solution of the resulting yellow syrup (101.6 g.) in dichloromethane-hexane (1:1) was passed through a column of magnesium silicate (FLORISIL) and stripped of solvent, affording 5α-androst-2-eno[3,2-b]furan-17β-ol (the compound of Formula IV wherein X-Y is

Z is H and Q is H) as a white solid (42.6 g., 37% yield). In one of two other preparations the product crystallized from methylene chloride as a white to off-white hydrated (4:1) crystalline solid having m.r. 135°-137° C. and in the other from dimethylformamide-water as a white unsolvated crystalline solid having m.r. 156°-157.5 C.

D. A solution of part (20.0 g.) of the product of part C of this example, dihydropyran (8.07 g.) and p-toluenesulfonic acid (1.3 g.) in dichloromethane (150 ml.) was stirred for 1.5 hours at room temperature, then poured into ice-water containing sodium bicarbonate. More dichloromethane was added. The dichloromethane layer was separated, washed with water, dried over magnesium sulfate and stripped of dichloromethane, affording 17β-[(tetrahydro-2H-pyran-2-yl)oxy]-5α-androst-2-eno[3,2-b]furan (the compound of Formula IV wherein X-Y is

Z is H and Q is tetrahydropyranyl; 23.1 g., 91% yield).

E. Under nitrogen with stirring at room temperature tetramethylethylendiamine (17.43 g.) and butyllithium (2.6M in hexane, 58 ml.) were added to a solution of 17β-[(tetrahydro-2H-pyran-2-yl)oxy]-5α-androst-2-eno[3,2-b]furan (the product of part D of this example, 29.0 g.) in dry ether (600 ml.). After 30 minutes methyl disulfide (14.13 g.) was added. Stirring was continued overnight, then the resulting mixture was neutralized with saturated aqueous ammonium chloride solution. The ether layer was separated, washed with water, dried over magnesium sulfate and stripped of ether, affording 5'-methylthio-17β-[(tetrahydro-2H-pyran-2-yl)oxy]-5α-androst-2-eno[3,2-b]furan (the compound of Formula II wherein R is CH₃, X-Y is

Z is H and Q is tetrahydropyranyl; 34.1 g.).

F. A solution of the entire product of part E of this example and p-toluenesulfonic acid (2.5 g.) in ethanol (95%, 500 ml.) was heated on a steam bath with stirring for one hour, concentrated and poured into ice-water. The resulting mixture was extracted with dichloromethane. The dichloromethane extract was washed with water and aqueous sodium bicarbonate solution and stripped of dichloromethane. A solution of the resulting yellow oil in dichloromethane was passed through a magnesium silicate (FLOROSIL) column with dichloromethane and ethyl acetate and stripped of solvents. Recrystallization of the resulting crystals (17.3 g.) from methanol gave 5'-methylthio-5α-androst-2-eno[3,2-b]furan-17β-ol (the compound of Formula II wherein R is CH$_3$, X-Y is

Z is H and Q is H) as a light yellow-crystalline solid (14.1 g., 54% yield for this step and the previous step combined; m.r. 95°–97° C.).

G. Under nitrogen at 0° C. in two runs a solution of 5'-methylthio-5α-androst-2-eno[3,2-b]furan-17β-ol (the product of part F of this example, 8.9 g., 36.3 g.) and m-chloroperbenzoic acid (9.5 g., 43.1 g.) in dichloromethane (100 ml., 400 ml.) was stirred for one hour. Aqueous sodium sulfite solution (10%) was then added. The dichloromethane layer was separated, washed with water and saturated aqueous sodium bicarbonate solution, dried over magnesium sulfate and stripped of dichloromethane. A solution of the combined products (8.1 g., 38.5 g.) in ethyl acetate was passed through a silica gel column. The eluate was subjected to HPLC on silica gel using hexane-ethyl acetate (70:30) as eluant, affording as the major component 5'-methylsulfonyl-5α-androst-2-eno[3,2-b]furan-17β-ol (the compound of Formula I wherein R is CH$_3$, X-Y is

and Z is H; 15.5 g., 33% yield corrected for 3.1 g. of the corresponding tetrahydropyranyl ether isolated as the minor component; tetrahydropyranyl was removed therefrom using p-toluenesulfonic acid and 95% ethanol). Recrystallization of part (5.5 g.) of the product from ethyl acetate-hexane gave an off-white crystalline solid having m.r. 144°–146°.

EXAMPLE 2

A. Under nitrogen with stirring at 0° C. a solution of 5'-methylsulfonyl-5α-androst-2-eno[3,2-b]furan-17β-ol (the product of part G of example 1, 11.5 g.) in dry dichloromethane (100 ml.) was added dropwise to a suspension of pyridinium chlorochromate (9.5 g.) in dry dichloromethane (100 ml.). Stirring was continued for four hours at room temperature. The supernatant solution was decanted and the tarry residue was triturated twice with dichloromethane (200 ml. each time). The combined decantings were washed first with hydrochloric acid (2N) and then with water until neutral, dried over magnesium sulfate, passed through a column of magnesium silicate (FLORISIL) and stripped of dichloromethane, affording 5'-methylsulfonyl-5α-androst-2-eno[3,2-b]furan-17-one (the compound of Formula III wherein R is CH$_3$ and X-Y is

(9.1 g., 80% yield).

B. Under nitrogen with stirring at from −60° C. to −50° C. a solution of dimethylsulfoxide (31 ml.) in dichloromethane (40 ml.) was added dropwise to a solution of trifluoroacetic anhydride (31 ml.) in dichloromethane (100 ml.). After 30 minutes a solution of 5α-androst-2-eno[3,2-b]furan-17β-ol (the product of part C of example 11.4 g.) in dichloromethane (100 ml.) was added dropwise. The temperature was allowed to rise to and remain at −30° C. for two hours. Diisopropylethylamine (135 ml.) was then added at from −60° C. to −40° C. The temperature was allowed to rise to room temperature. The solution was allowed to stand for three days, washed first with saturated aqueous sodium bicarbonate solution and then with hydrochloric acid (1N), dried over magnesium sulfate and stripped of volatiles. Crystallization of the resulting oily solid (20 g.) from ethanol (95%) gave 5'-methylthio-5α-androst-2-eno[3,2-b]furan-17-one (the compound of Formula II wherein R is CH$_3$, X-Y is

and Q and Z taken together are a bond) as a pale tan crystalline solid (4.5 g., 35% yield, m.r. 128°–130° C.).

C. Under nitrogen with stirring at from −15° C. to +5° C. a solution of potassium peroxymonosulfate (OXONE) (49.5%, 55.35 g.) in water (200 ml.) was added to a solution of 5'-methylthio-5α-androst-2-eno[3,2-b]furan-17-one (the product of part B of this example, 16 g.) in methanol (400 ml.). One hour thereafter the temperature was allowed to rise to room temperature and to remain thereat overnight. The mixture was poured into water (3 l.). The resulting solid was collected by filtration, washed with water, dried (4.8 g.) and purified by column chromatography on silica get (Kieselgel, 200 g.). Elution with hexane-ethyl acetate (70:30) afforded 5'-methylsulfonyl-5α-androst TM 2-eno[3,2-b]furan-17-one (the same product as that of part A of this example) as a white crystalline solid (4 g., 23% yield, m.r. 220°–222° C.).

D. Under nitrogen with stirring at −78 C. acetylene gas (purified by bubbling through two sulfuric acid traps and an alumina column) was bubbled through dry tetrahydrofuran (80 ml.) for one hour. A solution of n-butyllithium in hexane (2.6M, 9.6 ml.) was added during 20 minutes with continued acetylene bubbling. Ten minutes thereafter a suspension of 5'-methylsulfonyl-5α-androst-2-eno[3,2-b]furan-17-one (the product of part C of this example 8.4 g.) in dry tetrahydrofuran (15 ml.) was slowly added. Stirring was continued for one hour at −78° C. and then for two hours at room temperature. The mixture was poured into saturated aqueous ammonium chloride solution. The tetrahydrofuran layer was separated, dried over magnesium sulfate and stripped of tetrahydrofuran. Trituration of the residue (9.1 g.) with ether gave a crystalline solid (7.3 g.), recrystallization of which from dichloromethane-ether (1:1) gave 5'-methylsulfonyl-5α-pregn-2-en-20-yno[3,2-b]furan-17β-ol (the compound of Formula I wherein R is CH$_3$, X-Y is

and Z is C≡CH) as a white crystalline solid (5.6 g., 62% yield, m.r. 159°–161° C.).

EXAMPLE 3

A. Under nitrogen with stirring at room temperature tetramethylethylenediamine (18.2 g.) then butyllithium (2.5M in hexane, 62.8 ml.) were added to a solution of 17β-[(tetrahydro-2H-pyran-2-yl)oxy]-5α-androst-2-eno[3,2-b]furan (the product of part D of example 1, 25.0 g.) in dry ether (450 ml.). After 30 minutes a solution of ethyl disulfide (19.2 g.) in dry ether (40 ml.) was added and stirring was continued over the weekend. Saturated aqueous ammonium chloride solution was added. The ether layer was separated, dried over magnesium sulfate and stripped of volatiles, affording crude 5'-ethylthio-17β-[(tetrahydro-2H-pyran-2-yl)oxy]-5α-androst-2-eno[3,2-b]furan (the compound of Formula II wherein R is CH₃CH₂, X-Y is

Z is H and Q is tetrahydropyranyl; 30.1 g.).

B. In two runs a solution of crude 5'-ethylthio-17β-[(tetrahydro-2H-pyran-2-yl)oxy]-5α-androst-2-eno[3,2-b]furan (the product of part A of this example; 13.7 g., 12.9 g.) and p-toluenesulfonic acid (1.0 g., 1.0 g.) in ethanol (95%, 200 ml., 200 ml.) was heated on steam bath for about one hour, concentrated and poured into ice-water. The resulting mixture was extracted with dichloromethane. The dichloromethane extract was washed with water and saturated aqueous sodium bicarbonate solution, dried over magnesium sulfate, concentrated, passed through a column of magnesium silicate (FLORISIL) with dichloromethane as eluant and stripped of dichloromethane. Purification of part (16 g.) of the resulting combined products (10.4 g., 6.1 g.) by HPLC on silica gel using hexane-ethyl acetate (80:20) as eluant and trituration of the resulting product (9.5 g.) with pentane gave 5'-ethylthio-5α-androst-2-eno[3,2-b]furan-17β-ol (the compound of Formula II wherein R is CH₃CH₂, X-Y is

Z is H and Q is H) as an off-white crystalline solid (7.5 g., 37% yield for this step and the previous step combined, m.r. 105°–107° C.).

C. Under nitrogen with stirring at −78° C., m-chloroperbenzoic acid (26.0 g.) was added to a solution of crude 5'-ethylthio-5α-androst-2-eno[3,2-b]furan-17β-ol (the product of part B of this example, 25.0 g.) in dichloromethane (400 ml.). The temperature was maintained at −78° C. for 30 minutes, then allowed to rise to room temperature and remain there for about one hour. Aqueous sodium sulfite solution (10%) was then added. The dichloromethane layer was separated, washed with water and saturated aqueous sodium bicarbonate solution, dried over magnesium sulfate, passed through a silica gel column and stripped of dichloromethane. Purification of the residue (20.0 g.) by HPLC on silica gel using hexane-ethyl acetate (70:30) as eluant gave 5'-ethylsulfonyl-5α-androst-2-eno[3,2-b]furan-17β-ol (the compound of Formula I wherein R is CH₃CH₂, X-Y is

and Z is H; 10.6 g., 56% yield for this step and the previous two steps combined, m.r. 95°–97° C.), recrystallization of which from ethyl acetate-hexane (1:1) gave a pale yellow crystalline solid (6.1 g.) of unchanged melting range.

EXAMPLE 4

A. Under nitrogen with stirring at room temperature tetramethylethylenediamine (13.9 g.) then butyllithium (2.6M in hexane, 46 ml.) were added to a solution of 17β-[(tetrahydro-2H-pyran-2-yl)oxy]-5α-androst-2-eno[3,2-b]furan (the product of part D of example 1, 19.0 g.) in dry ether (550 ml.). After 30 minutes a solution of diisopropyl disulfide (17.98 g.) in dry ether (30 ml.) was added and stirring was continued overnight. Saturated aqueous ammonium chloride solution was added. The ether layer was separated, dried over magnesium sulfate and stripped of volatiles, affording crude 5'-(1-methylethylthio)-17β-[(tetrahydro-2H-pyran-2-yl)oxy]-5α-androst-2-eno[3,2-b]furan (the compound of Formula II wherein R is (CH₃)₂CH, X-Y is

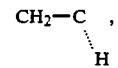

Z is H and Q is tetrahydropyranyl; 24.0 g.).

B. A solution of crude 5'-(1-methylethylthio)-17β-[(tetrahydro-2H-pyran-2-yl)oxy]-5α-androst-2-eno[3,2-b]furan (the product of part B of this example, 22.6 g.) and p-toluenesulfonic acid (2.0 g.) in ethanol (95%, 400 ml.) was heated on a steam bath for about one hour, concentrated and poured into ice-water. The resulting mixture was extracted with dichloromethane. The dichloromethane extract was washed with water and saturated aqueous sodium bicarbonate solution, dried over magnesium sulfate, concentrated, passed through a column of magnesium silicate (FLORISIL) with dichloromethane and stripped of dichloromethane. Trituration of the residue (21.0 g.) with pentane gave 5'-(1-methylethylthio)-5α-androst-2-eno[3,2-b]furan-17β-ol (the compound of Formula II wherein R is (CH₃)₂CH, X-Y is

Z is H and Q is H) as a white crystalline solid (8.1 g., 46% yield for this step and the previous step combined, m.r. 131°–133° C.).

C. Under nitrogen with stirring at 0° C., a solution of m-chloroperbenzoic acid (28.1 g.) in dichloromethane was added to a solution of crude 5'-(1-methylethylthio-5α-androst-2-eno[3,2-b]furan-17β-ol (the product of part B of this example, 24.4 g.) in dichloromethane (400 ml.). The temperature was maintained at 0° C. for 30 minutes, then allowed to rise to room temperature and remain there for about one hour. Aqueous sodium sulfite solution (10%) was then added. The dichloromethane layer was separated, washed with water and saturated aqueous sodium bicarbonate solution and again with water, dried over magnesium sulfate and stripped of dichloromethane. Purification of the residue by HPLC on silica gel using hexane-ethyl acetate (70:30) as eluant and trituration of the resulting product with hexane gave 5′-(1-methylethylsulfonyl)-5α-androst-2-eno[3,2-b]furan-17β-ol (the compound of Formula I wherein R is (CH$_3$)$_2$CH, X-Y is $$CH_2\!\!-\!\!\overset{\vdots}{C}$$
$$H$$

and Z is H) as an off-white crystalline solid (7.5 g., 37% yield for this step and the previous two steps combined), m.r. 138°–139° C.).

Antiandrogenic Properties of the Compounds

Utility of the compounds of Formula I as antiandrogenic agents was evaluated in two tests, the in vitro rat prostate androgen receptor competition assay and the in vivo test for antiandrogenic activity in the castrated immature male rat.

In the rat prostate androgen receptor competition assay prostate glands from 24 hr. castrated adult male rats weighing approximately 250 g. were homogenized in aqueous pH 7.4 buffer containing triaziquone (10 mM), sodium molybdate (20 mM), 1,4-dithiothreitol (2.0 mM) and glycerol (10%). The homogenate was centrifuged at the equivalent of 105,000 g. for 1 hr. Aliquots of the supernatant liquid (cytosol) were incubated with methyltrienolone labelled with tritium in the 17α-methyl (5 nM final concentration) in either the absence or presence of increasing concentrations (10$^{31}$ 9–10$^{-5}$M) of unlabelled methyltrienolone as a reference or of a test compound for 1 hr. or overnight (approximately 18 hr.) at 4° C. Triamcinolone acetonide (1 μM) was added to the cytosol before incubation to block the low affinity binding of labelled methyltrienolone to progesterone and glucocorticoid receptors. After the 1 hr. or 18 hr. incubation period an aqueous suspension of dextran (T-70, 0.05%)-coated charcoal (1%) was added to the incubation mixture and incubation was continued for 5 min. The incubation mixture was centrifuged to remove charcoal (nonprotein)-bound labelled methyltrienolone. The supernatant was separated and its radioactivity was counted to determine the concentration of protein-bound labelled methyltrienolone. The relative binding affinity was calculated as the concentration of test compound required to reduce the concentration of protein-bound labelled methyltrienolone by 50% as a percentage relative to unlabelled methyltrienolone. Androgens including the naturally occurring testosterone and 5α-dihydrotestosterone (stanolone) and the synthetic methyltrienolone and stanozolol show high relative binding affinities and 1 hr./18 hr. relative binding affinity ratios close to unity. In general antiandrogens including flutamide and cyproterone acetate show lower relative binding affinities and 1 hr./18 hr. relative binding affinity ratios greater than 10.

In the test for antiandrogenic activity in the castrated immature male rat weanling male rats were castrated and, beginning one week later, grouped by body weight and medicated orally with an ethanol (10%)-cottonseed oil suspension of test compound and testosterone propionate (0.8 mg./kg.) for 10 consecutive days. On the day following the last medication the rats were weighed and sacrificed. The ventral prostate gland, seminal vesicles and levator ani muscle of each rat were removed, blotted and weighed. Antiandrogenic potency is defined as the AED$_{50}$, which is the approximate dose of test compound required to inhibit testosterone propionate stimulated prostate weight gain by 50%. Test compounds which did not inhibit prostate weight gain by 50% but nevertheless showed significant (P<0.01) inhibition at a dose of 100 mg./kg. are considered active and are assigned an AED$_{50}$ value of >100.

The following results were obtained.

| Product of Example | Relative Binding Affinity | | Antiandrogenic Potency AED$_{50}$ (mg./kg. Orally) |
|---|---|---|---|
| | 1 Hr. | 18 Hr. | |
| 1G | 17.6 | 4.3 | ca. 100 |
| 2D | 2.2 | 0.2 | 9.4 |
| 3C | 5.4 | 1.2 | ca. 100 |
| 4C | 5.4 | 1.2 | >100 |

In the process of effecting an antiandrogenic response in a mammal the antiandrogenically effective amount of the compound of Formula I can be estimated from the foregoing test results. This aspect of the invention is contemplated to be carried out in any mammal having a disease or disorder reversible by use of an antiandrogenic agent, preferably in the human male in the treatment of benign prostatic hypertrophy or prostatic cancer or in the human female in the treatment of polycystic ovarian disease or both or in other human disease or metabolic disorder amenable to treatment with an antiandrogenic agent. It can be carried out using the compound of Formula I alone, but is preferably carried out using a composition comprising the compound of Formula I and a pharmaceutically acceptable vehicle.

The Compositions

The compositions in accordance with the second composition of matter aspect of the invention can be prepared for oral, parenteral, rectal or vaginal administration and can be in solid or liquid dosage form including capsules, tablets, suppositories, solutions, suspensions and emulsions. Conventional pharmaceutically acceptable vehicles and techniques are used in preparing these dosage forms.

We claim:

1. A compound having the structural formula

Formula I

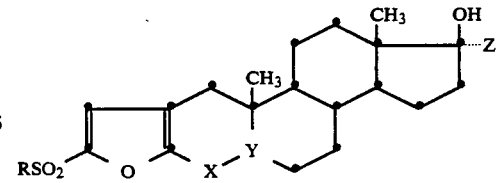

wherein
R is CH$_3$, CH$_3$CH$_2$, CH$_3$CH$_2$CH$_2$ or (CH$_3$)$_2$CH;
X-Y is

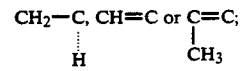

and
Z is H, CH$_3$, CH$_2$CH$_3$, C≡CH or CH=CH$_2$.

2. A compound according to claim 1 wherein X-Y is

3. A compound according to claim 2 wherein Z is H.

4. 5'-Methylsulfonyl-5α-androst-2-eno[3,2-b]furan-17β-ol according to claim 3.

5. 5'-Ethylsulfonyl-5α-androst-2-eno[3,2-b]furan-17β-ol according to claim 3.

6. 5'-(1-Methylethylsulfonyl)-5α-androst-2-eno[3,2-b]furan-17β-ol according to claim 3.

7. A compound according to claim 2 wherein Z is C≡CH.

8. 5'-Methylsulfonyl-5α-pregn-2-en-20-yno[3,2-b]furan-17β-ol according to claim 7.

9. The process for effecting an antiandrogenic response in a mammal which comprises administering to the mammal an antiandrogenically effective amount of a compound of Formula I according to claim 1.

10. The process for effecting an antiandrogenic response in a mammal which comprises administering to the mammal an antiandrogenically effective amount of a compound of Formula I according to claim 4.

11. The process for effecting an antiandrogenic response in a mammal which comprises administering to the mammal an antiandrogenically effective amount of a compound of Formula I according to claim 5.

12. The process for effecting an antiandrogenic response in a mammal which comprises administering to the mammal an antiandrogenically effective amount of a compound of Formula I according to claim 6.

13. The process for effecting an antiandrogenic response in a mammal which comprises administering to the mammal an antiandrogenically effective amount of a compound of Formula I according to claim 8.

14. A composition which comprises an antiandrogenically effective concentration of a compound of Formula I according to claim 1 and a pharmaceutically acceptable vehicle.

* * * * *